United States Patent [19]

Gaffar et al.

[11] Patent Number: 5,089,255
[45] Date of Patent: Feb. 18, 1992

[54] DENTAL REMINERALIZATION

[75] Inventors: Abdul Gaffar, Princeton; James Mellberg, Pottersville; John Blake-Haskins, Piscataway, all of N.J.

[73] Assignee: Colgate-Palmolive Company, Piscataway, N.J.

[21] Appl. No.: 649,208

[22] Filed: Jan. 25, 1991

Related U.S. Application Data

[63] Continuation of Ser. No. 371,145, Jun. 26, 1989, abandoned.

[51] Int. Cl.⁵ .......................... A61K 7/16; A61K 7/18
[52] U.S. Cl. ...................................... 424/52; 424/673; 424/676
[58] Field of Search ...................... 424/49–58, 424/673, 676

[56] References Cited

U.S. PATENT DOCUMENTS

| | | | |
|---|---|---|---|
| 3,932,604 | 1/1976 | Barth | 424/49 |
| 3,970,747 | 7/1976 | Barth | 424/52 |
| 4,233,288 | 11/1980 | Cornell | 424/52 |
| 4,254,101 | 3/1981 | Denny | 424/52 |
| 4,284,650 | 8/1981 | Goupil | 424/49 |
| 4,314,990 | 2/1982 | Denny et al. | 424/52 |
| 4,340,583 | 7/1982 | Wason | 424/52 |
| 4,515,772 | 5/1985 | Parran et al. | 424/57 |
| 4,590,066 | 5/1986 | Parran et al. | 424/52 |
| 4,701,319 | 10/1987 | Woo | 424/52 |
| 4,806,339 | 2/1989 | Parran et al. | 424/52 |
| 4,822,599 | 4/1989 | Mitra | 424/52 |
| 4,842,847 | 6/1989 | Amjad | 424/52 |
| 4,885,155 | 12/1989 | Parran et al. | 424/52 |

FOREIGN PATENT DOCUMENTS

| | | |
|---|---|---|
| 0138705 | 4/1985 | European Pat. Off. |
| 0251146 | 1/1988 | European Pat. Off. |
| 30776 | 9/1976 | United Kingdom. |
| 2204487A | 11/1988 | United Kingdom. |

OTHER PUBLICATIONS

Vissink et al., C.A.102; 160408s (1985) of Caries Res. 19(3); 212–218 (1985), "Rehardening properties ... on Softened Human Enamel Effects of Sorbitol, Xylitol ...".

Rolla et al., C.A. 108; 81860d (1988) of EP251146, Jan. 7, 1988.

*Primary Examiner*—Shep K. Rose
*Attorney, Agent, or Firm*—Robert L. Stone; Murray M. Grill; Robert C. Sullivan

[57] ABSTRACT

A method is disclosed for remineralizing demineralized portions of teeth by treatment with a non-astringent composition containing about 10–20% xylitol, and at least one fluoride ion-providing compound in a total amount sufficient to provide about 150 ppm to about 1800 ppm of fluoride ions, with sodium fluoride providing a predominant proportion of such fluoride ions.

6 Claims, No Drawings

DENTAL REMINERALIZATION

This application is a continuation of application Ser. No. 07/371,145, filed June 26, 1989, now abandoned.

FIELD OF THE INVENTION

The present invention relates to oral compositions in the form of dentrifices and mouthwashes providing improved remineralization effects.

BACKGROUND OF THE INVENTION

In the mouth, there is a natural equilibrium between hydroxyapatite being dissolved from the enamel of teeth, on the one hand, and hydroxyapatite being formed on or in the teeth from substances occurring naturally in the saliva, on the other. This equilibrium is shifting continuously. Among other factors, it is determined by diet and physical condition. If the equilibrium is such that hydroxyapatite is dissolved, a cariogenic condition arises which is referred to as demineralization. If the equilibrium is such that hydroxyapatite is being formed in demineralized enamel, this is referred to as remineralization. By remineralization, pre-existing tooth decay and caries can be reduced or eliminated by natural means.

It has long been known that fluoride-providing compounds, even in low concentrations, promote the remineralization process and thereby reduce pre-existing carious conditions in the tooth structure.

Xylitol has been disclosed in patent and literature publications for the treatment of dental structures to provide sweetened non-cariogenic compositions, control dental plaque, prophylactic prevention of occurrence of carious conditions, and/or remineralization of pre-existing carious conditions. Barth U.S. Pat. No. 3,932,604 and its divisional U.S. Pat. No. 3,970,747, are directed to dentifrices containing substantial amounts of xylitol as a non-cariogenic sweetener/humectant, and discloses formulations also containing sodium monofluorophosphate; no remineralizing effect is disclosed. Hoffman-LaRoche Irish Patent Application 307/76, filed Feb. 16, 1976 and opened to public inspection Sept. 1, 1976 (based on Swiss Application 2158/75), discloses oral compositions containing xylitol, but no fluoride, for remineralizing dental caries. EP Publication No. 0138705, published in Patent Bulletin 85/17, discloses anti-caries compositions containing xylitol and mixtures of at least two fluoride salts providing at least 2,000 up to 20,000 ppm total fluoride ion. EP Publication No. 0251146, published Jan. 7, 1988 in Patent Bulletin 88/01, discloses oral compositions having a dental plaque preventing, and thus caries-prophylactic, activity containing a synergistic mixture of at least one fluorine compound, at least one zinc ion releasing compound (astringent), and xylitol.

It is an object of this invention to provide a new and improved method of remineralizing demineralized portions of tooth structures. Another object of the invention is to provide such a process yielding unexpectedly improved remineralization effects. Other objects and advantages will appear as the description proceeds.

SUMMARY OF THE INVENTION

The attainment of one or more of the above objects is made possible by the present invention which includes a method for remineralizing demineralized portions of tooth structures comprising applying to such portions a non-astringent oral composition in the form of a dentifrice or mouthwash containing approximately by weight, 10% to 20% of xylitol and at least one fluoride ion-providing compound in a total amount sufficient to provide 150 ppm to 1800 ppm, preferably 200 to 1200 ppm, of fluoride ions, with sodium fluoride providing a predominant proportion of such fluoride ions.

DETAILED DESCRIPTION OF THE INVENTION

As indicated above, the compositions employed in the present invention are non-astringent, i.e. they are devoid of zinc salts which introduce problems of mouth feel and taste and tend to interfere with the desired remineralizing mechanism, for example by reacting with, complexing, precipitating or otherwise modifying the essential xylitol and sodium fluoride in the presently employed compositions.

In the method of the present invention, the defined combination of xylitol and fluoride ion-providing compounds, employed in amounts within the indicated weight ranges and in relative proportions or ratios predetermined to achieve optimum remineralization effects, have been unexpectedly found to coact synergistically to yield substantially better remineralization results than those obtainable with compositions containing the individual xylitol and fluoride ion-providing compounds.

The fluoride ion-providing compounds optionally present singly or in any mixtures thereof in the compositions employed in the present invention in addition to the essential sodium fluoride are well known as anti-caries agents. They may be fully or at least slightly but sufficiently water soluble to provide the required fluoride ions, organic or inorganic, and are characterized by their ability to release fluoride ions in water or saliva and by their freedom from undesired reaction with the other components of the oral compositions employed herein.

Inorganic fluoride ion-providing compounds include metal, alkali metal, alkaline earth metal and ammonium salts, as for example potassium fluoride, ammonium bifluoride, calcium fluoride, a copper fluoride such as cuprous fluoride, barium fluoride, sodium fluorosilicate, ammonium fluorosilicate, sodium fluorozirconate, sodium monofluorophosphate, aluminum mono- and difluorophosphate, fluorinated sodium calcium pyrophosphate, stannous fluoride, lithium fluoride, cesium fluoride, aluminum fluoride, cupric fluoride, indium fluoride, stannous fluorozirconate, ferric fluoride, nickel fluoride, palladium fluoride, silver fluoride, zirconium fluoride, and the like and mixtures thereof.

Organic fluoride ion-providing compounds include hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, $\Delta^{8-9}$octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N;-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyldimethylammonium fluoride, N-(B-hydroxydodecyl)trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-cicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and the like and mixtures thereof.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 5:1 to 18:1 and more preferably about 10:1 to about 15:1. The total amount of water-alcohol mixture in this type of preparation is typically in the range of from about 50% to about 99% by weight of the preparation, often combined with about 5 to about 40% of humectant, some or all of which may be xylitol.

The pH of such liquid and other preparations of the invention is generally in the range of from about 4.5 to about 10 and typically from about 5.5 to 9. The pH is preferably in the range of from about 6 to about 8.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the dentifrice composition may be substantially solid or pasty in character, such as toothpowder, a dental tablet, a toothpaste (cream), or a dental gel. The vehicle of such solid or pasty dentifrice preparations typically contains an orally or dentally acceptable polishing material for use in conjunction with a brushing of the teeth. Examples of such polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 4,070,510 of Dec. 15, 1962 such as melamine-, phenolic-, and urea-formaldehydes, and cross-linked polyepoxides and polyesters. Preferred polishing materials include crystalline silica having particle sizes of up to about 5 microns, and a mean particle size of up to about 1.1 microns, and a surface area of up to about 50,000 cm.$^2$/gm., silica gel or colloidal silica, and complex amorphous alkali metal alumino-silicate.

When visually clear gels are desired, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated in Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste or gel and from about 70% to about 99% in toothpowder or tablet.

In a toothpaste, dental cream or gel, the liquid vehicle is typically water in concentrations of about 2% to about 50% and mixed with about 0.2 to about 5 parts of humectant per part by weight of the water. The active xylitol may function as part or all of the humectant. Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration, about 3–30 wt. % of water, 0 to about 80 wt. % of glycerine, and about 20–80 wt. % of sorbitol is preferably employed.

Toothpastes (creams) and gels typically contain a natural or synthetic binder, thickener or gelling agent in proportions of about 0.1 to about 10, preferably about 0.5 to about 5, wt. %. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitable labelled packages. Thus, a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

One or more organic surface-active agents are used in the compositions of the present invention to achieve increased wetting, foaming and prophylactic action, assist in achieving thorough and complete dispersion of the composition throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anti-calculus agents, and/or ammoniated material such as urea, diammonium phosphate, and mixtures thereof. These adjuvants, where present, are incorporated in the preparations in amounts which do not substantially adversely affect the properties and characteristics desired. Significant amounts of zinc and other metal salts and materials, generally soluble, which would complex with the active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, dextrose, levulose, sorbitol, d-tryptophan, dihydrochalcones, sodium cyclamate, perillartine, APM (aspartyl phenyl alanine, methyl ester), saccharine and the like. The active xylitol may constitute part or all of the sweetening agent. Suitably, flavor and sweetening agents may together comprise from about 0.1% to 5% or more of the preparation.

In practicing the method of this invention, the defined composition in the usual amounts employed with conventional oral compositions is preferably applied to demineralized portions of tooth structures in the oral cavities of caries-troubled consumers, by brushing in the case of toothpastes, creams, gels and powders and by "swishing" in the case of mouthwashes, for from about 1 to about 5 minutes 1 to 3 times daily until achievement of the desired degree of remineralization. The composition is typically removed by rinsing with water after each application.

The method of the invention may also be employed professionally using the compositions in the form of coherent thickened pastes or gels for local, topical application to demineralized portions of tooth structures.

The following examples are further illustrative of the nature of the present invention but it is to be understood that the invention is not limited thereto. All amounts and proportions referred to herein and in the appended claims are by weight and temperatures are in degrees C. unless otherwise indicated.

EXAMPLE 1

| Mouthwash Composition | |
|---|---|
| Ingredient | Parts |
| Deionized water | 57.3824 |
| Xylitol | 20.0000 |
| Glycerine | 7.5000 |
| Sorbitol (70% Aqueous Solution) | 7.5000 |
| Ethanol | 4.9984 |
| Pluronic F-108* | 0.9992 |
| Pluronic F-127* | 0.9992 |
| Sodium Benzoate | 0.5000 |
| Sodium Fluoride | 0.0484** |
| FD&C Blue No. 1 | 0.0400 |
| FD&C Yellow No. 5 | 0.0200 |
| Benzoic Acid | 0.0100 |
| Flavor | 0.0024 |
| TOTAL | 100.0000 |

*Polyoxyethyleneated polyoxypropylene nonionic block polymer surfactants.
**Supplies 225 ppm fluoride ion.

EXAMPLE 2

The mouthwash composition of Example 1 is tested in vivo for in situ remineralization of artificial caries lesions in humans employing the methodology described in Mellberg et al, J. Dent. Res. 65 1078–1083 (1983), which description is incorporated here by reference thereto. Results of the tests are as follows:

| Composition Employed | % Remineralization |
|---|---|
| (a) Example 1 | 17.4 |
| (b) Example 1 minus Xylitol | 11.3 |
| (c) Example 1 minus fluoride | −4.7 |
| (d) Placebo | −1.7 |

These results establish that use of the Example 1 mouthwash composition (a) in the method of this invention unexpectedly achieves substantially and significantly better remineralization than use of either the same composition minus xylitol (b), i.e. with fluoride alone, or the same composition minus fluoride (c), i.e. with xylitol alone, or the placebo (d).

EXAMPLE 3

| Ingredient | Dentifrice Composition Formulation (Parts) | | |
|---|---|---|---|
| | A | B | C (Placebo) |
| (1) Polyethylene glycol 600 | 3.000 | 3.000 | 3.000 |
| Carboxymethyl Cellulose | 0.350 | 0.350 | 0.350 |
| (2) Sorbitol (70% Aqueous Soln) | 63.117 | 53.117 | 63.360 |
| NaBenzoate | 0.500 | 0.500 | 0.500 |
| TiO$_2$ | 0.500 | 0.500 | 0.500 |
| Tetra Sodium Pyrophosphate | 0.500 | 0.500 | 0.500 |
| Xylitol | — | 10.000 | — |
| (3) Deionized Water | 6.000 | 6.000 | 6.000 |
| NaF | 0.243 | 0.243 | — |
| Na Saccharin | 0.200 | 0.200 | 0.200 |
| (4) Zeodent 113* | 18.000 | 18.000 | 18.000 |
| Sylodent 15** | 5.500 | 5.500 | 5.500 |
| Flavor | 0.890 | 0.890 | 0.890 |
| (5) Sodium Lauryl Sulfate | 1.200 | 1.200 | 1.200 |
| | 100.000 | 100.000 | 100.000 |

*Precipitated silica polishing agent.
**Silica thickening agent.

This dentifrice composition is prepared by mixing parts (1), (2), (3), (4) and (5) in sequence.

EXAMPLE 4

The dentifrice compositions of Example 3 are tested in vivo in a rat caries assay described in A. Gaffar et al, Calcif. Tissue Res. 35 S62–S65 (1983), which description is incorporated herein by reference thereto: Results of the assay are as follows:

| Dentifrice Treatment | N | Mean/Rat | | |
|---|---|---|---|---|
| | | Initial Caries | Fissure Caries | Smooth Surface Caries |
| Placebo (C) | 10 | 11.5 | 8.5 | 15.7 |
| NaF (A) | 10 | 4.7 | 1.0 | 2.7 |
| NaF/10% Xylitol (B) | 10 | 2.7 | 0.2 | 0.5 |

These results establish that the use of Example 3 dentifrice composition (B) in the method of the invention is unexpectedly substantially and significantly ($P<0.05$) more effective against caries than use of the same composition without xylitol (A), i.e. with sodium fluoride alone, and the placebo (C).

This invention has been described with respect to certain preferred embodiments and it will be understood that modifications and variations thereof obvious to those skilled in the art are to be included within the spirit and purview of this application and the scope of the appended claims.

We claim:

1. A method of remineralizing demineralized portions of tooth structures of caries-troubled consumers comprising applying to such portions a non-astringent oral dentifrice compositin in the form of a toothpaste or gel containing, approximately by weight, 10% to 20% of xylitol and at least one fluoride ion-providing compound in a total amount sufficient to provide 150 ppm to 1800 ppm of fluoride ions, with sodium fluoride providing the sole or a predominant portion of such fluoride ions, said composition being free of significant amounts of astringent zinc salts which react with, complex, or precipitate xylitol and sodium fluoride, the amounts of xylitol and fluoride ion-providing compounds employed in the composition providing in combination substantially better remineralizing effects than those provided by the individually employed xylitol and fluoride ion-providing compounds.

2. A method according to claim 1 wherein said composition contains sodium fluoride as the sole fluoride ion-providing compound.

3. A method according to claim 1 wherein said composition is in the form of a dentifrice further containing a dentally acceptable polishing agent.

4. A method according to claim 3 wherein said composition further contains a binding, gelling or thickening agent.

5. A method according to any of claims 1 to 4 wherein said composition contains an orally acceptable vehicle and a humectant selected from the group consisting of glycerine, propylene glycol, sorbitol, polypropylene glycol and polyethylene glycol.

6. A method according to any of claims 1 to 4 wherein said composition has a pH of about 4.5 to about 10.

* * * * *